United States Patent [19]

Lin

[11] Patent Number: 5,582,612
[45] Date of Patent: Dec. 10, 1996

[54] VERTEBRAL FIXING AND RETRIEVING DEVICE HAVING CENTRALLY TWO FIXATION

[76] Inventor: Chih-I Lin, 14292 Spring Vista La., Chino Hills, Calif. 91709

[21] Appl. No.: 431,741

[22] Filed: May 1, 1995

[51] Int. Cl.⁶ .................................................. A61B 17/56
[52] U.S. Cl. .................................................. 606/61; 606/60
[58] Field of Search .............................. 606/17, 60, 61, 606/69, 72, 73

[56] References Cited

U.S. PATENT DOCUMENTS

| | | | |
|---|---|---|---|
| 5,116,334 | 5/1992 | Cozad et al. | 606/61 |
| 5,330,473 | 7/1994 | Howland | 606/61 |
| 5,387,212 | 2/1995 | Yuan et al. | |
| 5,470,333 | 11/1995 | Ray | 606/61 |

Primary Examiner—Michael Powell Buiz
Assistant Examiner—Mark S. Leonardo
Attorney, Agent, or Firm—Bacon & Thomas

[57] ABSTRACT

A vertebral fixation device includes a fixation main body, two fixation rods and a rotatable clamping block. The fixation main body is made up of a fixation base having a fixation hole. Located respectively at both ends of the fixation base is a fixation block having an arcuate surface capable of holding one of the two fixation rods in conjunction with one of two arcuate recesses of the rotatable clamping block. The rotatable clamping block is provided at the bottom thereof with a retaining projection engageable securely with the fixation hole of the fixation main body.

16 Claims, 8 Drawing Sheets

VERTEBRAL FIXING AND RETRIEVING DEVICE HAVING CENTRALLY TWO FIXATION

FIELD OF THE INVENTION

The present invention relates generally to a surgical device for treating a deformed vertebra, and more particularly to a vertebral fixing and retrieving device which is provided centrally with two fixation rods.

BACKGROUND OF THE INVENTION

It is a well-known fact that the surgical treatment of a deformed vertebra can be often complicated by a slight vertebral movement. For example, the deformation of a central rod of the vertebral fixation system is often brought about by the slight vertebral movement. For this reason, the conventional central rod fixation system for treating a deformed vertebra, such as the one disclosed in U.S. Pat. No. 5,387,212 by this inventor of the present invention, is provided with a longitudinal auxiliary fixation system which is intended to fix each of the horizontal fixing and retrieving members of the central rod fixation system.

Such a conventional central rod fixation system as described above is defective in design in that it is rather complicated in construction, and that its implementation can prolong the surgical duration, and further that it is unsuitable for use in a surgical treatment in which two bone screws must be fastened onto both sides of a vertebra at a rather short interval.

SUMMARY OF THE INVENTION

It is therefore the primary objective of the present invention to provide a vertebral fixing and retrieving system with two central fixation rods. The system of the present invention is intended to overcome all of the shortcomings of the conventional system described above.

The foregoing objective of the present invention is attained by a vertebral fixing and retrieving device, which comprises a fixation main body, two fixation rods, and a rotatable clamping block.

The fixation main body is made up of a fixation base which is provided at both ends thereof or both sides thereof with a vertebral fixation means and is further provided with a fixation hole located at the center thereof or in the vicinity of the center thereof. In addition, the fixation base is provided respectively at both ends thereof with a fixation block.

The two fixation rods are held respectively by the two fixation blocks of the fixation base of the fixation main body.

The rotatable clamping block is provided at the bottom thereof with a retaining projection engageable with the fixation hole of the fixation main body. The rotatable clamping block is further provided at both ends thereof with two arcuate recesses opposite in location to each other for holding securely the two fixation rods in conjunction with the two fixation blocks.

The fixation base of the fixation main body is composed of a base plate having the two fixation blocks which are located respectively at both ends thereof and are curved inwardly in opposite directions. The base plate is provided with a fixation hole which is located at the center thereof or in the vicinity of the center thereof. The vertebral fixation means of the fixation main body of the present invention is similar in construction to the conventional vertebral fixation means, such as the fixation plate/block having a fixation slot, which is engaged with the bone screw fastened onto the vertebra. A suitable fixation means is the one disclosed in U.S. patent application Ser. No. 08/431,740, filed on the same day of this application, by this inventor of the present invention. The total number of the vertebral fixation means of the present invention may range between two and four, preferably two. If two vertebral fixation means are employed in the surgical treatment, these two vertebral fixation means may be located respectively at one side or one end of the two fixation blocks. If these two vertebral fixation means are composed of two fixation plates and two bone screws which are fastened onto the same vertebra at a relatively short interval, these two vertebral fixation means are preferably and respectively located at one side of the fixation blocks, preferably at the same side of the fixation blocks. In case these two bone screws are fastened onto the same vertebra at a relatively long interval, these vertebral fixation means are preferably and respectively located at both ends of the two fixation blocks.

The fixation blocks of the fixation main body of the present invention are provided respectively with an arcuate inner surface having a radius which is preferably equal to the radius of the fixation rod.

The fixation rod of the present invention is similar in construction to the fixation rod of the vertebral retrieving device of the prior art. The fixation rod of the present invention may be provided with an auxiliary fixation means, such as a fixation cord, a fixation hook, etc.

As mentioned previously, the rotatable clamping block of the present invention is provided at the bottom thereof with a retaining projection engageable with the fixation hole of the fixation main body. The method by which the retaining projection is engaged securely with the fixation hole is similar to any conventional fastening method.

The two fixation rods of the present invention can be received respectively in a gap formed respectively between the two fixation blocks and the rotatable clamping block which is disposed in an upright position. As the rotatable clamping block is so turned that it is located in a horizontal position, the two fixation rods are then held firmly in the gaps formed between the rotatable clamping block and the two fixation blocks. If necessary, the base plate of the fixation main body and the rotatable clamping block may be provided respectively with an arresting means capable of preventing the engagement of the base plate and the rotatable clamping block two fixation rods from being loosened by the vertebral movement.

The foregoing objective, features and advantages of the present invention will be more readily understood upon a thoughtful deliberation of the following detailed description of the present invention in conjunction with the accompanying drawings.

DETAILED DESCRIPTION OF THE EMBODIMENTS

Figure 1A:
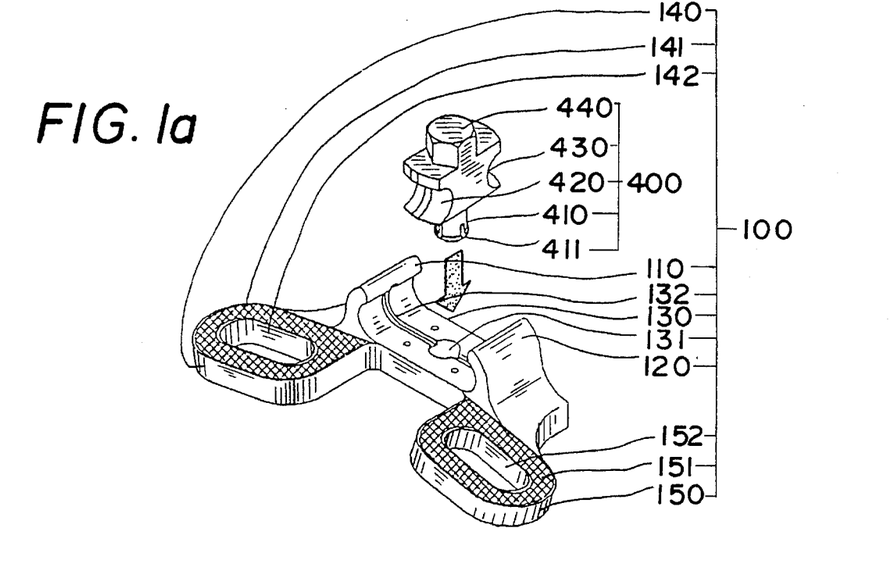
FIGS. 1a–1c are schematic views illustrating the fastening process of a first preferred embodiment of the present invention.

As shown in FIG. 1a, the present invention comprises a fixation main body 100, two fixation blocks 110 and 120, a base plate 130, two fixation plates 140 and 150 which are located respectively at the same side of the fixation blocks 110 and 120 and are provided respectively with fixation slot 142(152) having a rough surface 141(151) for fastening with a bone screw having dual threads. The base plate 130 is provided with a fixation hole 131 and an arresting mortise 132. The present invention further comprises a rotatable clamping block 400 which is provided with a retaining projection 410 and a fastening nut 440. The retaining projection 410 has a slit 411. The rotatable clamping block 400 is further provided with two arcuate recesses 420 and 430. The retaining projection 410 is thrust into the fixation hole 131 of the fixation main body 100 in such a manner that the slit 411 of the retaining projection 410 is so contracted that the retaining projection 410 is held securely by the fixation hole 131.

Figure 1B:
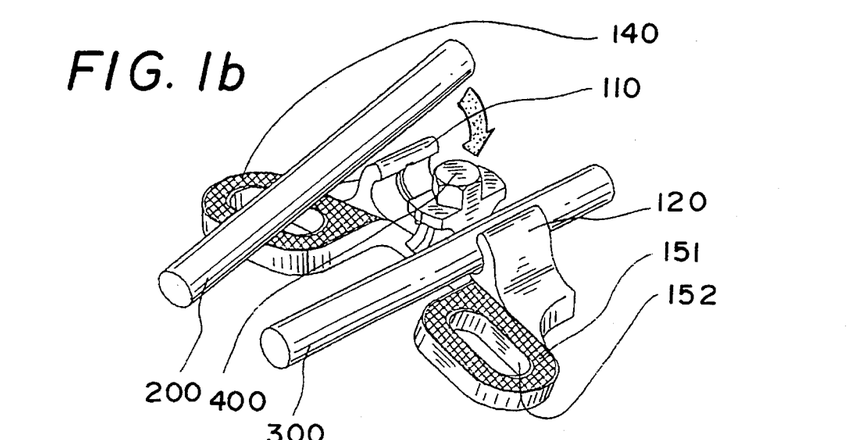

As shown in FIG. 1b, the present invention comprises two fixation rods 200 and 300, which are held respectively between the two arcuate recesses 420, 430 of the rotatable clamping block 400 and two fixation blocks 110, 120. The reference numerals of FIG. 1b are similar in definition to the like reference numerals of FIG. 1a.

Figure 1C:
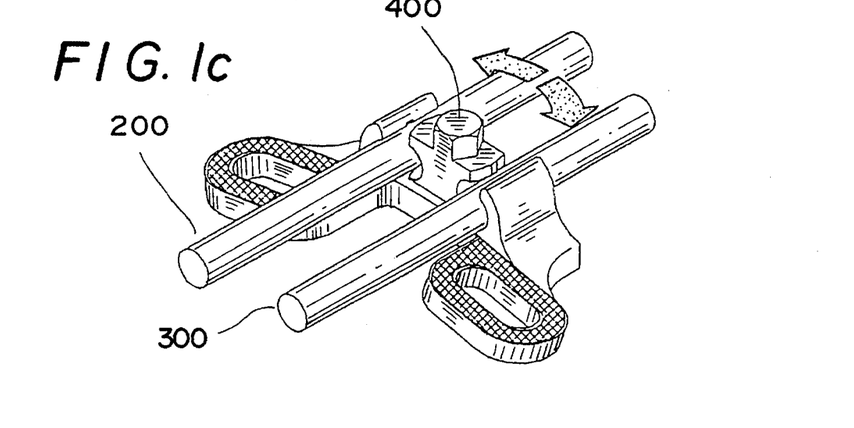

The reference numerals of FIG. 1c are similar in definition to the like reference numerals of FIGS. 1a and 1b. As shown in FIG. 1c, the rotatable clamping block 400 is so turned that the two fixation rods 200 and 300 are held firmly.

Figure 2A:
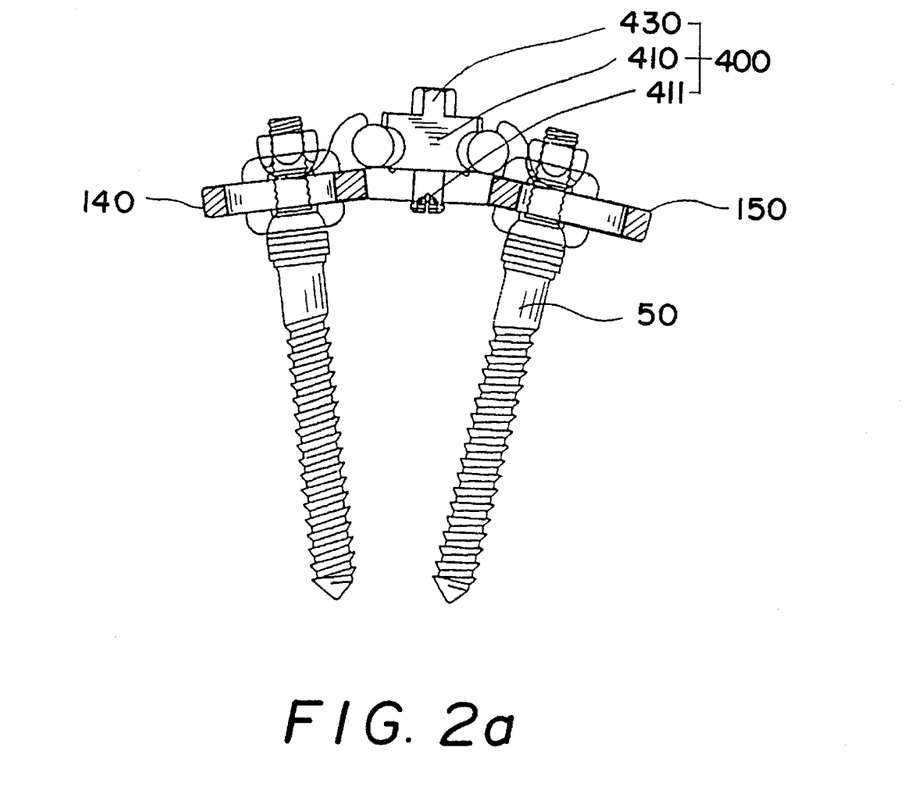
FIG. 2a shows a side elevational view of the first preferred embodiment in combination according to the present invention.

As shown in FIG. 2a, the vertebral fixing and retrieving device of the present invention is employed in conjunction with two double-threaded bone screws 500 invented by this inventor of the present invention. The reference numerals of FIG. 2a are similar in definition to the like reference numerals of FIGS. 1a–1c. The method by which the two bone screws 500 are fastened with the fixation plate 140 or 150 is illustrated in FIGS. 3a and 3b.

Figure 2B:
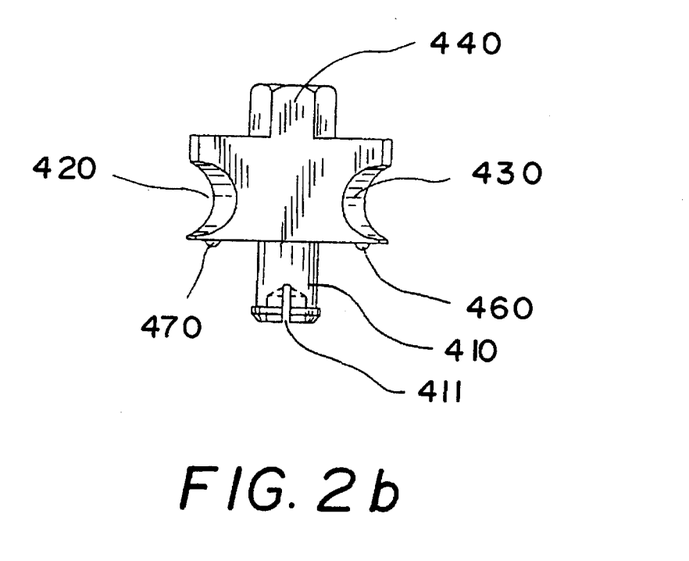
FIG. 2b shows a side elevational view of the rotatable clamping block as shown in FIG. 1.

As shown in FIG. 2b, the rotatable clamping block 400 of the present invention is provided with two arresting tenons 460 and 470 which are engaged with the arresting mortise 132 of the base plate 130. The reference numerals 410–440 of FIG. 2b are similar in definition to the like reference numerals of FIGS. 1a–1c.

Figure 3A:
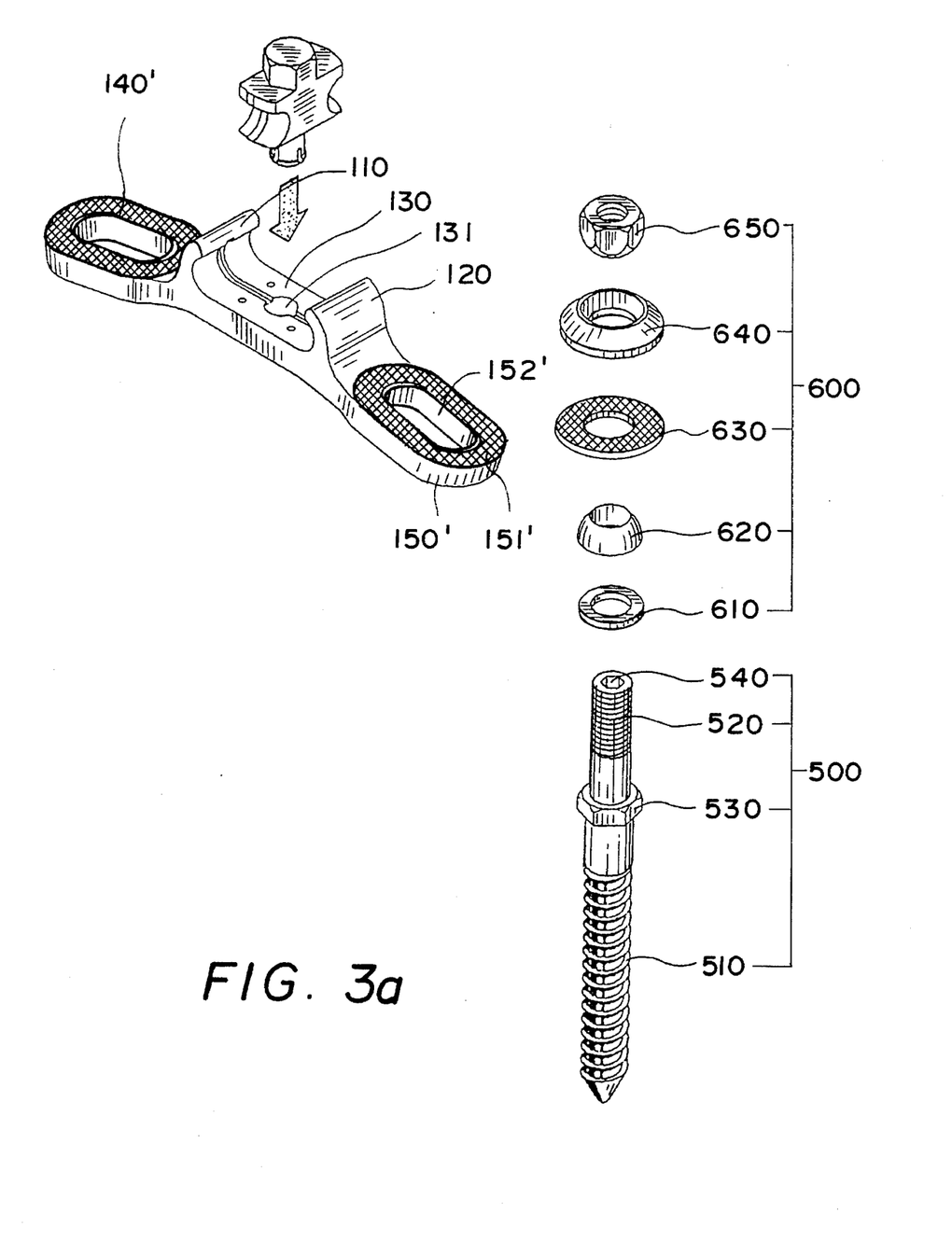
FIGS. 3a–3c are schematic views illustrating the fastening process of a second preferred embodiment of the present invention.

The reference numerals 110–152 of FIG. 3a are similar in definition to the like reference numerals of FIGS. 1a–1c. As shown in FIG. 3a, the two fixation plates 140 and 150 are located respectively at the ends of the two fixation blocks 110 and 120. The bone screw 500 is provided with a first threaded portion 510, a second threaded portion 520, an arresting portion 530, and a tool hole 540. The bone screw 500 is fastened with the fixation plate 150 by means of a fastening mechanism 600 which is provided with a height adjusting washer 610, a direction adjusting washer 620, two knurled direction-adjusting washers 630, 640, and a fastening nut 650.

Figure 3B:
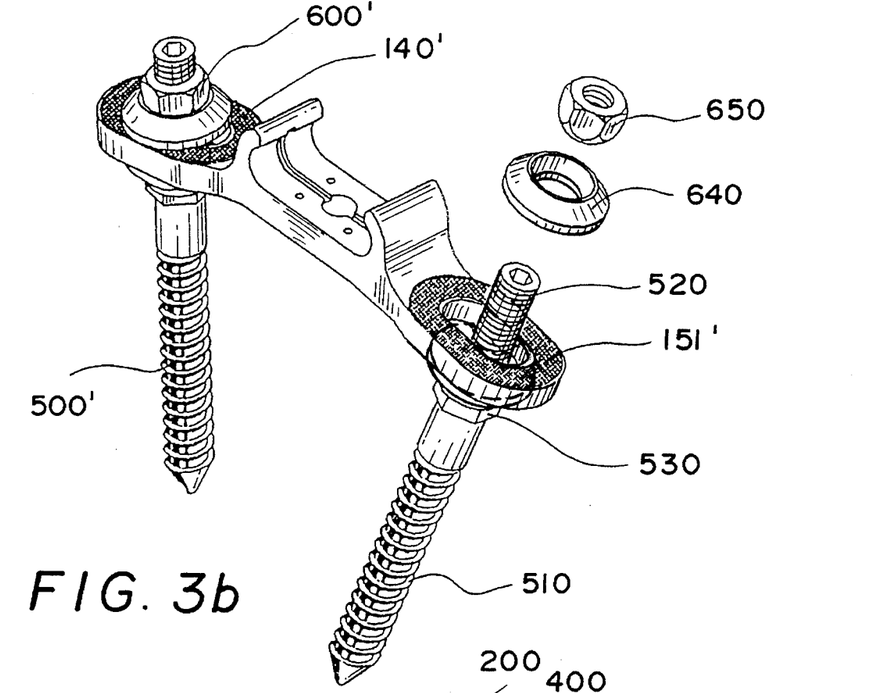

The reference numerals of FIG. 3b are similar in definition to the like reference numerals of FIG. 3a. As shown in FIGS. 3a and 3b, one ends of the bone screws 500 and 500' are fastened onto a vertebra (not shown in the drawing), and another ends of the bone screws 500 and 500' are fastened onto the fixation plates 140 and 150 respectively in the same manner. The bone screw 500 is joined orderly with the washers 610, 620, 630 before the fixation plate 150 is joined with the bone screw 500. Before fastening the fastening nut 650, the knurled direction-adjusting washer 640 must be fitted over the bone plate 150. Located at another end is an fastening mechanism 600' by means of which the bone screw 500' is fastened with the fixation plate 140.

Figure 3C:
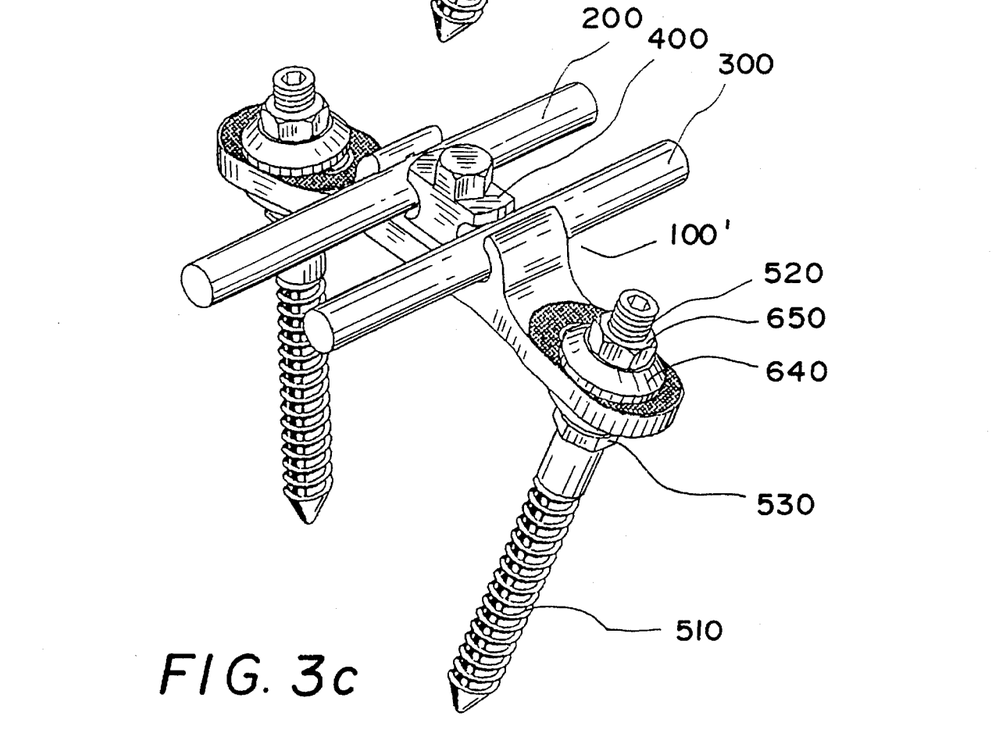

The reference numerals of FIG. 3c are similar in definition to the like reference numerals of FIGS. 1a–3b. The method by which the two fixation rods 200, 300, the rotatable clamping block 400 and the fixation main body 100 are fastened together is illustrated in FIGS. 1a–1c.

The advantages of the method of fastening the bone screw 500 with the fastening mechanism 600, as illustrated in FIGS. 3a–3c, are described explicitly in U.S. patent application Ser. No. 08/431,740, filed on the same day of this application, by this inventor of the present invention.

Figure 4:
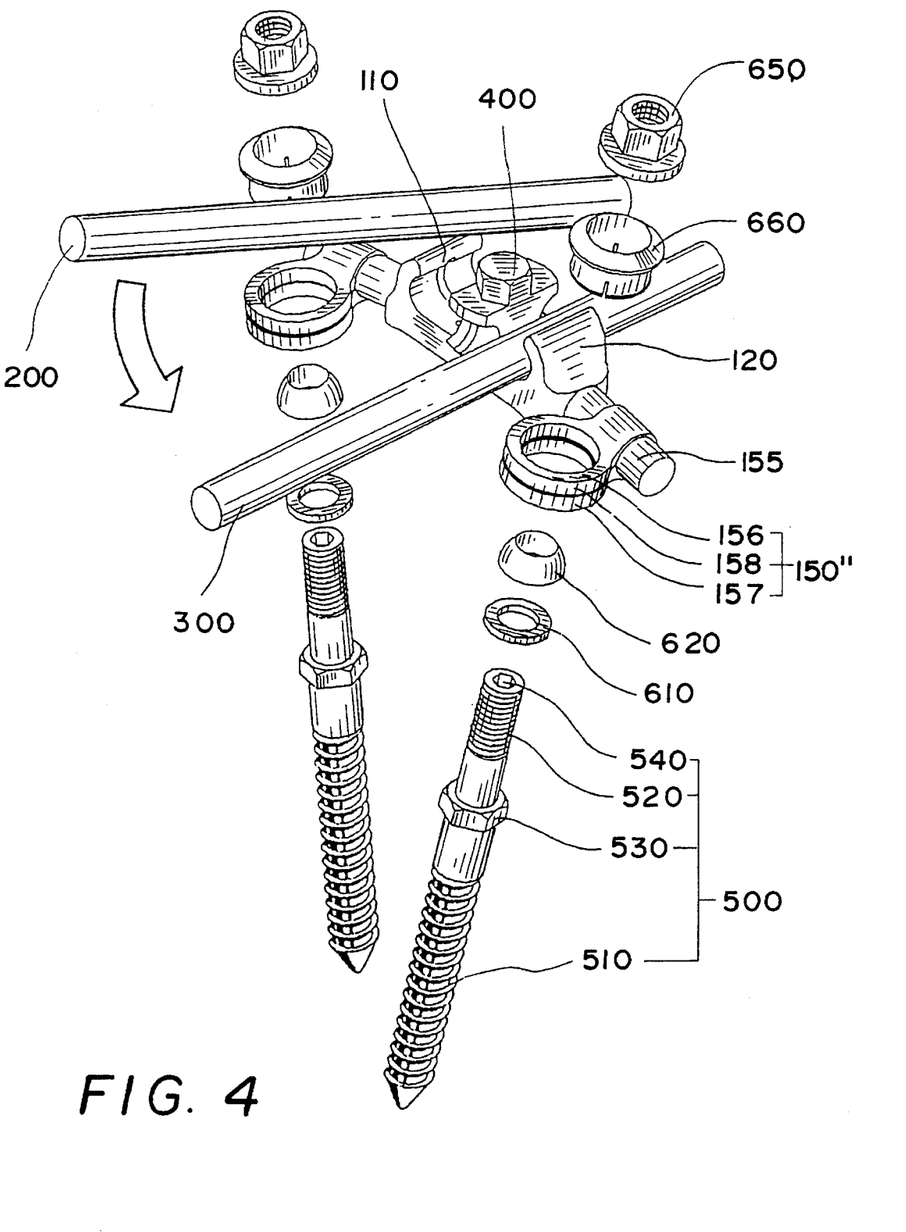
FIG. 4 shows an exploded view of a third preferred embodiment of the present invention.

The reference numerals of FIG. 4 are similar in definition to the like reference numerals of FIGS. 3a–3c. As shown in FIG. 4, the fixation base is provided respectively at both ends thereof with an extension rod 155 over which a fixation ring 150' is fitted. The fixation ring 150' is similar in function to the fixation plate 150 which is illustrated in FIG. 1a. The fixation ring 150' is provided with an upper fitting ring 156, a lower fitting ring 157, and a slit 158 therebetween. A fastening mechanism which is composed of a universal ring 660, the height adjusting washer 610, the direction adjusting washer 620 and the fastening nut 650 is used to fasten the fixation ring 150' to the extension rod 155. The fixation main body, two fixation rods 200, 300 and the rotatable clamping block 400 of the present invention can be fastened securely together in the same manner as illustrated in FIGS. 1a–1c.

Figure 5:
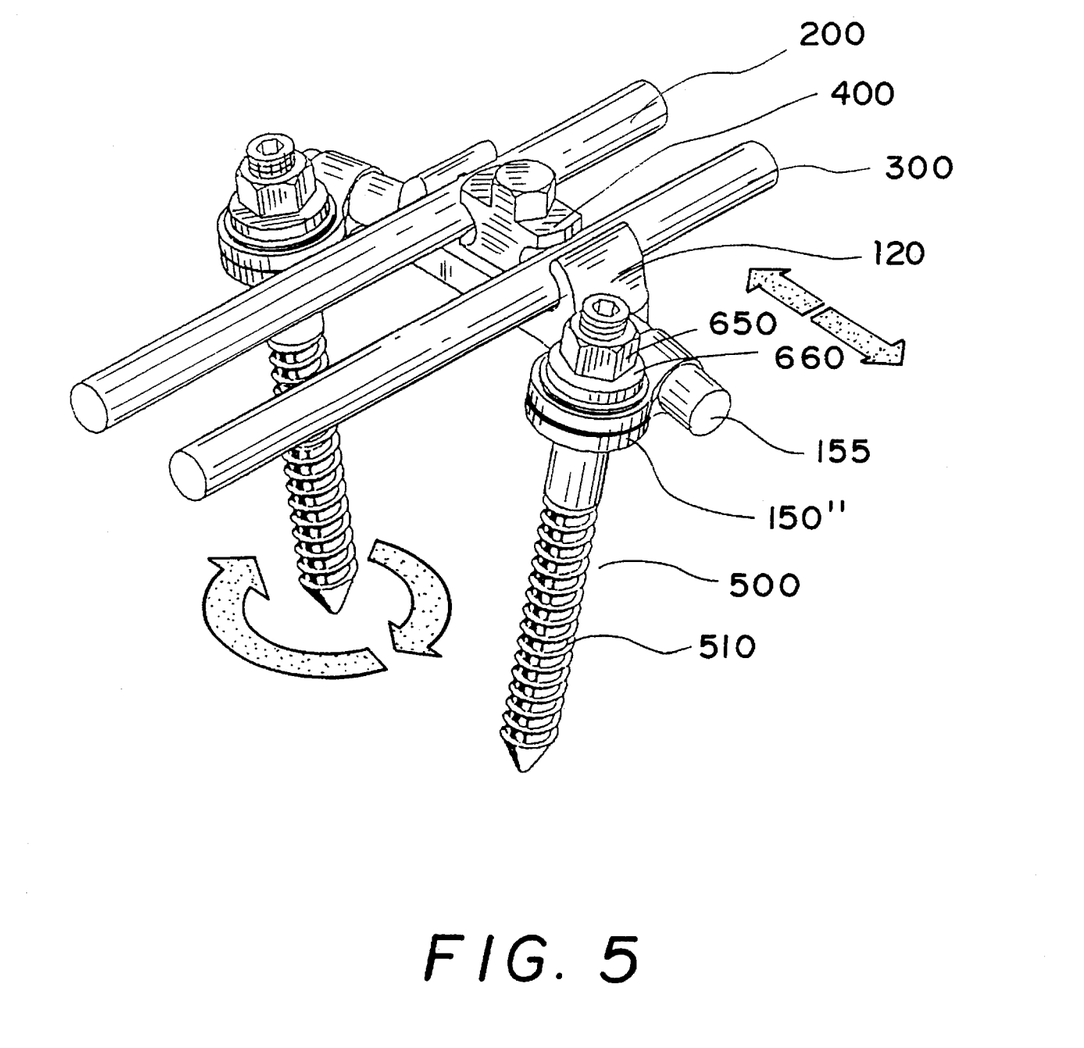
FIG. 5 shows a schematic view of the third preferred embodiment in combination according to the present invention.

The reference numerals of FIG. 5 are similar in definition to the like reference numerals of FIG. 4. The two arrows, which are arranged linearly, indicate that the location, at which the fixation ring 150' is fastened with the extension rod 155, is adjusted in accordance with the interval between the two bone screws. The two arrows, which are arranged circularly, indicate that the fastening angle formed by the bone screw 500 and the fixation ring 150' can be adjusted by means of the universal ring. For more details, please refer to U.S. patent application Ser. No. 08/431,739, filed on the same day of this application, by this inventor of the present invention.

Figure 6A:
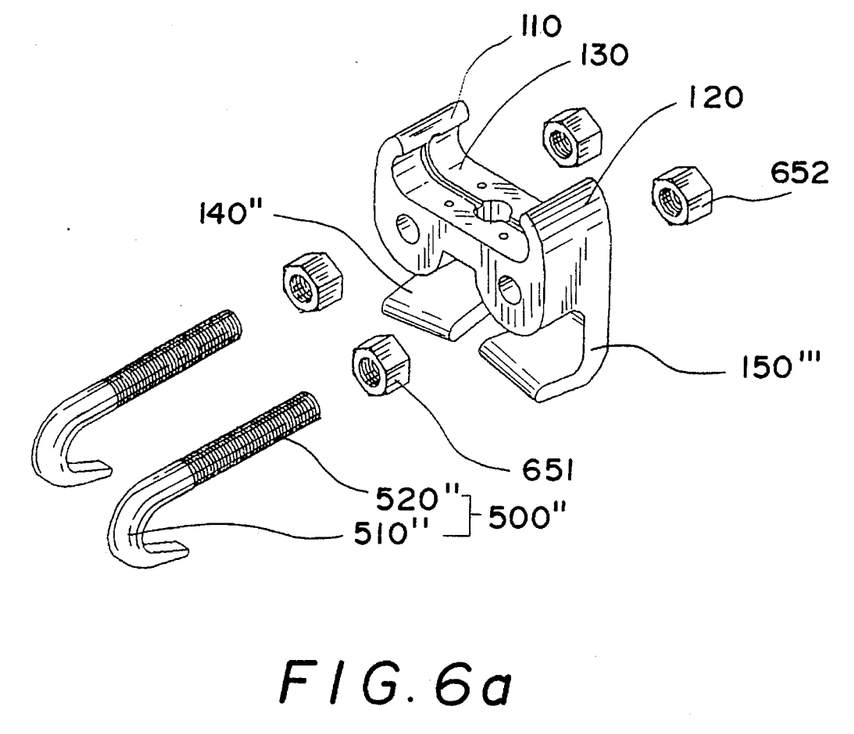
FIGS. 6a–6d are schematic views illustrating the fastening process of a fourth preferred embodiment of the present invention.
Figure 6B:
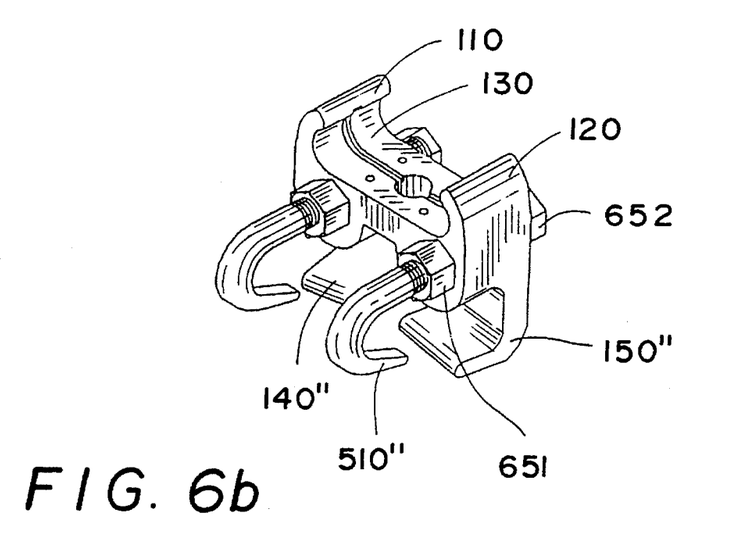

The fourth preferred embodiment of the present invention is illustrated in FIG. 6a in which the reference numerals of 110, 120 and 130 are similar in definition to the like reference numerals of FIG. 1a. The fourth preferred embodiment of the present invention is provided with bone hooks 140' and 150', which replace respectively the fixation plates 140 and 150 of the first preferred embodiment of the present invention shown in FIGS. 1a–1c. The bone hooks 140' and 150' are intended to cooperate respectively with two hooked threaded rods 500', each of which comprises a hooked portion 510' and a threaded portion 520', as shown in FIG. 6a. The threaded portion 520' of the hooked threaded rod 500' is engageable with nuts 651 and 652 for fastening the hooked threaded rod 500' with the fixation main body 100, as shown in FIG. 6b in which the reference numerals are similar in definition to the like reference numerals of FIG.

Figure 6C:
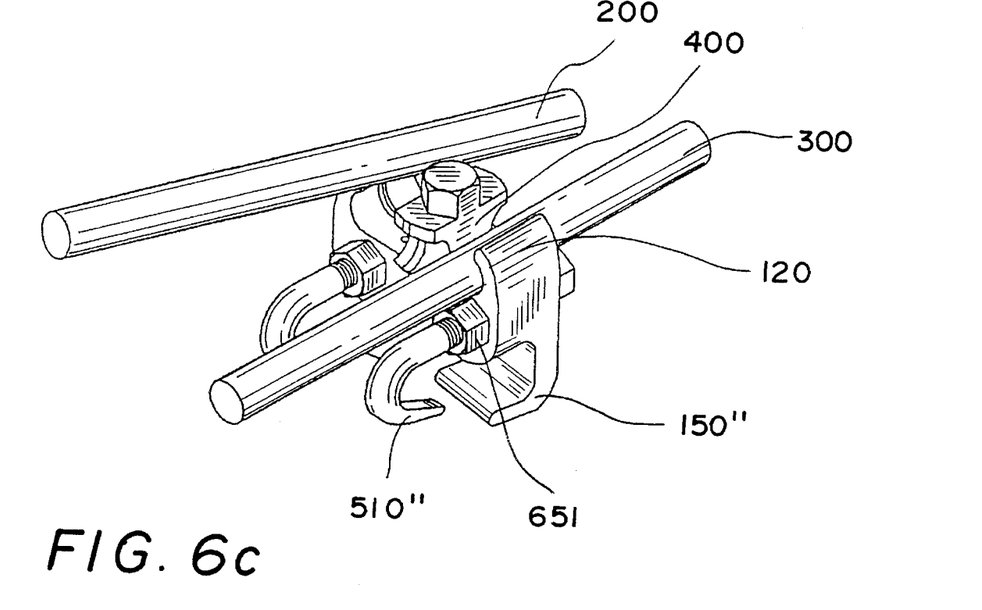
Figure 6D:
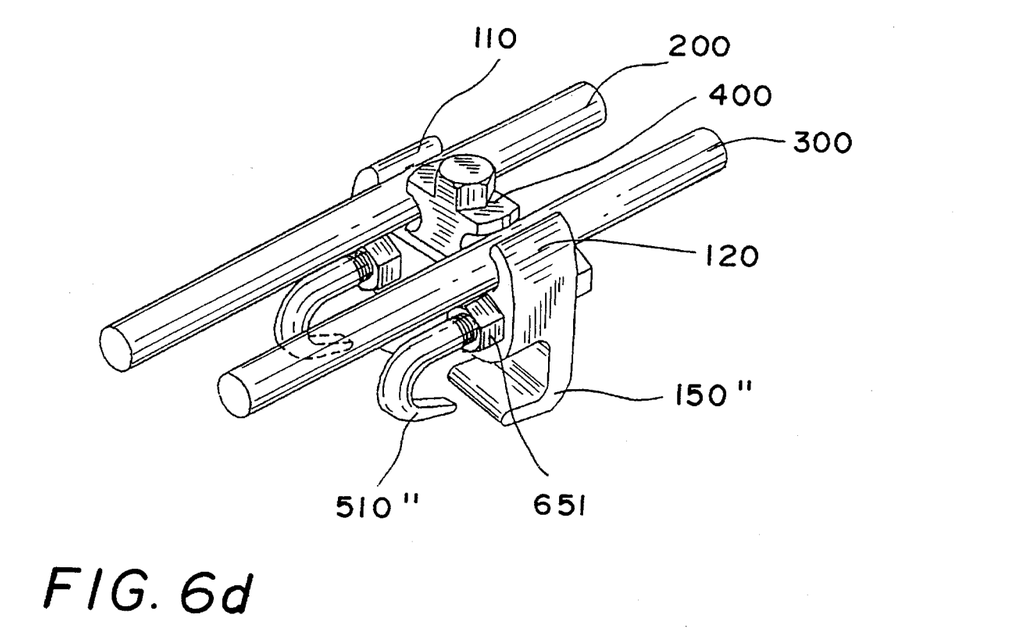

6a. The reference numerals of FIG. 6c are similar in definition to the like reference numerals of FIG. 1a and FIG. 6a. The method by which the two fixation rods 200 and 300 are fastened with the rotatable clamping block 400 is the same as that illustrated in FIGS. 1a–1c. The perspective view of the fourth preferred embodiment in combination is shown in FIG. 6d in which the reference numerals are similar in definition to the like reference numerals of FIGS. 6a–6c.

The embodiments of the present invention described above are to be regarded in all respects as merely illustrative and not restrictive. Accordingly, the present invention may be embodied in other specific forms without deviating form the spirit thereof. The present invention is therefore to be limited only by the scope of the following appended claims.

What is claimed is:

1. A vertebral fixing and retrieving device comprising:

a fixation main body having a fixation base which is provided respectively at both ends thereof with a fixation block and is further provided with a fixation hole located at a central portion thereof;

two fixation rods held respectively in an arcuate surface of said fixation block of said fixation main body; and a rotatable clamping block provided at a bottom thereof with a retaining projection engageable with said fixation hole of said fixation main body, said rotatable clamping block further provided respectively at both sides thereof with an arcuate recess capable of holding securely one of said two fixation rods in conjunction with said fixation block of said fixation main body by rotating said clamping block relative to said fixation main body to provide clearance for the insertion of said fixation rods between said clamping block and said fixation blocks and then again rotating said clamping block until each said fixation rod is positioned in a respective said arcuate recess of said clamping block.

2. The vertebral fixing and retrieving device as defined in claim 1, wherein said fixation base further comprises two spaced fixation plates.

3. The vertebral fixing and retrieving device as defined in claim 1, wherein said fixation base further comprises two spaced bone hooks.

4. The vertebral fixing and retrieving device as defined in claim 2, wherein said two fixation plates are located respectively at one side of said fixation blocks.

5. The vertebral fixing and retrieving device as defined in claim 2, wherein said two fixation plates are located respectively at both ends of said fixation base.

6. The vertebral fixing and retrieving device as defined in claim 1, wherein said fixation base is provided with an arresting mortise; and said rotatable clamping block is provided with an arresting tenon engageable with said arresting mortise of said fixation base.

7. The vertebral fixing and retrieving device as defined in claim 4, wherein said fixation base is provided with an arresting mortise; and said rotatable clamping block is provided with an arresting tenon engageable with said arresting mortise of said fixation base.

8. The vertebral fixing and retrieving device as defined in claim 5, wherein said fixation base is provided with an arresting mortise; and said rotatable clamping block is provided with an arresting tenon engageable with said arresting mortise of said fixation base.

9. A vertebral fixing and retrieving device comprising:

a fixation main body having a fixation base which is provided respectively at both ends thereof with a fixation block and is further provided with a fixation hole located at a central portion thereof;

two fixation rods held respectively in an arcuate surface of said fixation block of said fixation main body; and a clamping block provided at a bottom thereof with a retaining projection having a portion which constricts when initially inserted in said fixation hole and then expands after further insertion thereof such that said clamping block is connected to said fixation main body in a snap-fit manner, said clamping block further provided respectively at both sides thereof with an arcuate recess capable of holding securely one of said two fixation rods in conjunction with said fixation block of said fixation main body.

10. The vertebral fixing and retrieving device as defined in claim 9, wherein said fixation base further comprises two spaced fixation plates.

11. The vertebral fixing and retrieving device as defined in claim 9, wherein said fixation base further comprises two spaced bone hooks.

12. The vertebral fixing and retrieving device as defined in claim 10, wherein said two fixation plates are located respectively at one side of said fixation blocks.

13. The vertebral fixing and retrieving device as defined in claim 10, wherein said two fixation plates are located respectively at both ends of said fixation base.

14. The vertebral fixing and retrieving device as defined in claim 9, wherein said fixation base is provided with an arresting mortise; and said clamping block is provided with an arresting tenon engageable with said arresting mortise of said fixation base.

15. The vertebral fixing and retrieving device as defined in claim 12, wherein said fixation base is provided with an arresting mortise; and said clamping block is provided with an arresting tenon engageable with said arresting mortise of said fixation base.

16. The vertebral fixing and retrieving device as defined in claim 13, wherein said fixation base is provided with an arresting mortise; and said clamping block is provided with an arresting tenon engageable with said arresting mortise of said fixation base.

\* \* \* \* \*